(12) United States Patent
Rui et al.

(10) Patent No.: US 11,134,907 B2
(45) Date of Patent: Oct. 5, 2021

(54) SIGNAL PROCESSING METHOD AND IMAGING SYSTEM FOR SCATTER CORRECTION IN COMPUTED TOMOGRAPHY

(71) Applicant: General Electric Company, Schenectady, NY (US)

(72) Inventors: Xue Rui, Niskayuna, NY (US); Mingye Wu, ShangHai (CN); Yannan Jin, Niskayuna, NY (US); Peter Michael Edic, Niskayuna, NY (US); Bruno Kristiaan Bernard De Man, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 57 days.

(21) Appl. No.: 16/782,584

(22) Filed: Feb. 5, 2020

(65) Prior Publication Data

US 2020/0170599 A1 Jun. 4, 2020

Related U.S. Application Data

(62) Division of application No. 15/263,565, filed on Sep. 13, 2016, now Pat. No. 10,595,803.

(51) Int. Cl.
*A61B 6/00* (2006.01)
*A61B 6/03* (2006.01)

(52) U.S. Cl.
CPC .............. *A61B 6/482* (2013.01); *A61B 6/032* (2013.01); *A61B 6/4241* (2013.01); *A61B 6/50* (2013.01); *A61B 6/5205* (2013.01)

(58) Field of Classification Search
CPC ....... A61B 6/032; A61B 6/4241; A61B 6/482; G01N 23/046; G01N 2223/045
See application file for complete search history.

(56) References Cited

U.S. PATENT DOCUMENTS

| 7,283,605 | B2 * | 10/2007 | Sainath | G06T 11/005 |
| | | | | 378/207 |
| 8,483,471 | B2 * | 7/2013 | Wu | A61B 6/032 |
| | | | | 382/132 |
| 10,595,803 | B2 * | 3/2020 | Rui | A61B 6/482 |
| 2007/0147574 | A1 * | 6/2007 | De Man | A61B 6/482 |
| | | | | 378/4 |
| 2007/0189443 | A1 * | 8/2007 | Walter | A61B 6/504 |
| | | | | 378/4 |

(Continued)

*Primary Examiner* — Gandhi Thirugnanam
(74) *Attorney, Agent, or Firm* — Fletcher Yoder, P.C.

(57) ABSTRACT

A signal processing method is disclosed, which includes detecting a total intensity of X-rays passing through an object comprising multiple materials; obtaining at least one set of basis information of basis material information of the multiple materials and basis component information of photon-electric absorption basis component and Compton scattering basis component of the object; estimating a scatter intensity component of the detected X-rays based on the at least one set of basis information and the detected total intensity; and obtaining an intensity estimate of primary X-rays incident on a detector based on the detected total intensity and the estimated scatter intensity component. An imaging system adopting the above signal processing method is also disclosed.

20 Claims, 5 Drawing Sheets

(56) References Cited

U.S. PATENT DOCUMENTS

| | | | |
|---|---|---|---|
| 2008/0187195 A1* | 8/2008 | Kohler | G06T 11/006 382/128 |
| 2009/0080597 A1* | 3/2009 | Basu | A61B 6/482 378/5 |
| 2009/0208084 A1* | 8/2009 | Liu | A61B 6/4014 382/131 |
| 2010/0189212 A1* | 7/2010 | Zou | G06T 11/005 378/5 |
| 2013/0004050 A1* | 1/2013 | Wu | A61B 6/5205 382/132 |
| 2013/0058450 A1* | 3/2013 | Liu | A61B 6/032 378/7 |
| 2013/0336443 A1* | 12/2013 | Gagnon | A61B 6/4233 378/19 |
| 2016/0163072 A1* | 6/2016 | Koehler | G01N 23/046 382/132 |
| 2016/0302751 A1* | 10/2016 | Grant | A61B 6/50 |
| 2017/0215829 A1* | 8/2017 | Rui | A61B 6/032 |
| 2020/0170599 A1* | 6/2020 | Rui | A61B 6/4241 |
| 2020/0222024 A1* | 7/2020 | Edic | A61B 6/582 |

* cited by examiner

SIGNAL PROCESSING METHOD AND IMAGING SYSTEM FOR SCATTER CORRECTION IN COMPUTED TOMOGRAPHY

CROSS-REFERENCE TO RELATED APPLICATION

This application claims priority to and the benefit of U.S. patent application Ser. No. 15/263,565, entitled "SIGNAL PROCESSING METHOD AND IMAGING SYSTEM FOR SCATTER CORRECTION IN COMPUTED TOMOGRAPHY", filed Sep. 13, 2016, which is herein incorporated by reference in its entirety.

STATEMENT REGARDING FEDERALLY SPONSORED RESEARCH & DEVELOPMENT

This invention was made with US Government support under contract number 7R01HL111141-02 awarded by the US Department of Health and Human Services National Institutes of Health. The US Government has certain rights in the invention.

BACKGROUND

This disclosure relates generally to a signal processing technique, and more particularly to a signal processing method and an imaging system for scatter correction in computed tomography.

Non-invasive imaging technologies, such as computed tomography (CT), allow images of internal structures of an object to be obtained without performing an invasive procedure on the object. In a CT imaging system, scatter signal in the X-ray measurement can cause shading artifacts, reduce image resolution, and other artifacts which all degrade image quality. At the same time, the scatter signal from the object is one of the major sources of bias of the quantitative measurements from the reconstructed images of the CT imaging system.

Accordingly, it would be desirable to reduce or eliminate the impact of scatter from the object that to be measured. Therefore, an improved scatter correction method would improve CT image quality.

BRIEF DESCRIPTION

In one embodiment, the present disclosure provides a signal processing method. The method comprises: detecting a total intensity of X-rays passing through an object comprising multiple materials; obtaining at least one set of basis information of basis material information of the multiple materials and basis component information of photon-electric absorption basis component and Compton scattering basis component of the object; estimating a scatter intensity component of the detected X-rays based on the at least one set of basis information and the detected total intensity; and obtaining an intensity estimate of primary X-rays incident on a detector based on the detected total intensity and the estimated scatter intensity component.

In another embodiment, the present disclosure provides an imaging system. The system comprises a detector and a computer. The detector is configured for detecting a total intensity of X-rays passing through an object comprising multiple materials. The computer is configured for obtaining at least one set of basis information of basis material information of the multiple materials and basis component information of photon-electric absorption basis component and Compton scattering basis component of the object, estimating a scatter intensity component of the detected X-rays based on the at least one set of basis information and the detected total intensity, and obtaining an intensity estimate of primary X-rays incident on the detector based on the detected total intensity and the estimated scatter intensity component.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present disclosure will be described herein below with reference to the accompanying drawings. In the following description, well-known functions or constructions are not described in detail to avoid obscuring the disclosure in unnecessary detail.

Unless defined otherwise, technical and scientific terms used herein have the same meaning as is commonly understood by one of ordinary skill in the art to which this disclosure belongs. The terms "first", "second", "third" and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean either or all of the listed items. The use of "including," "comprising" or "having" and variations thereof herein are meant to encompass the items listed thereafter and equivalents thereof as well as additional items. In addition, the terms "connected" and "coupled" are not restricted to physical or mechanical connections or couplings, and can include electrical connections or couplings, whether direct or indirect.

Figure 1:
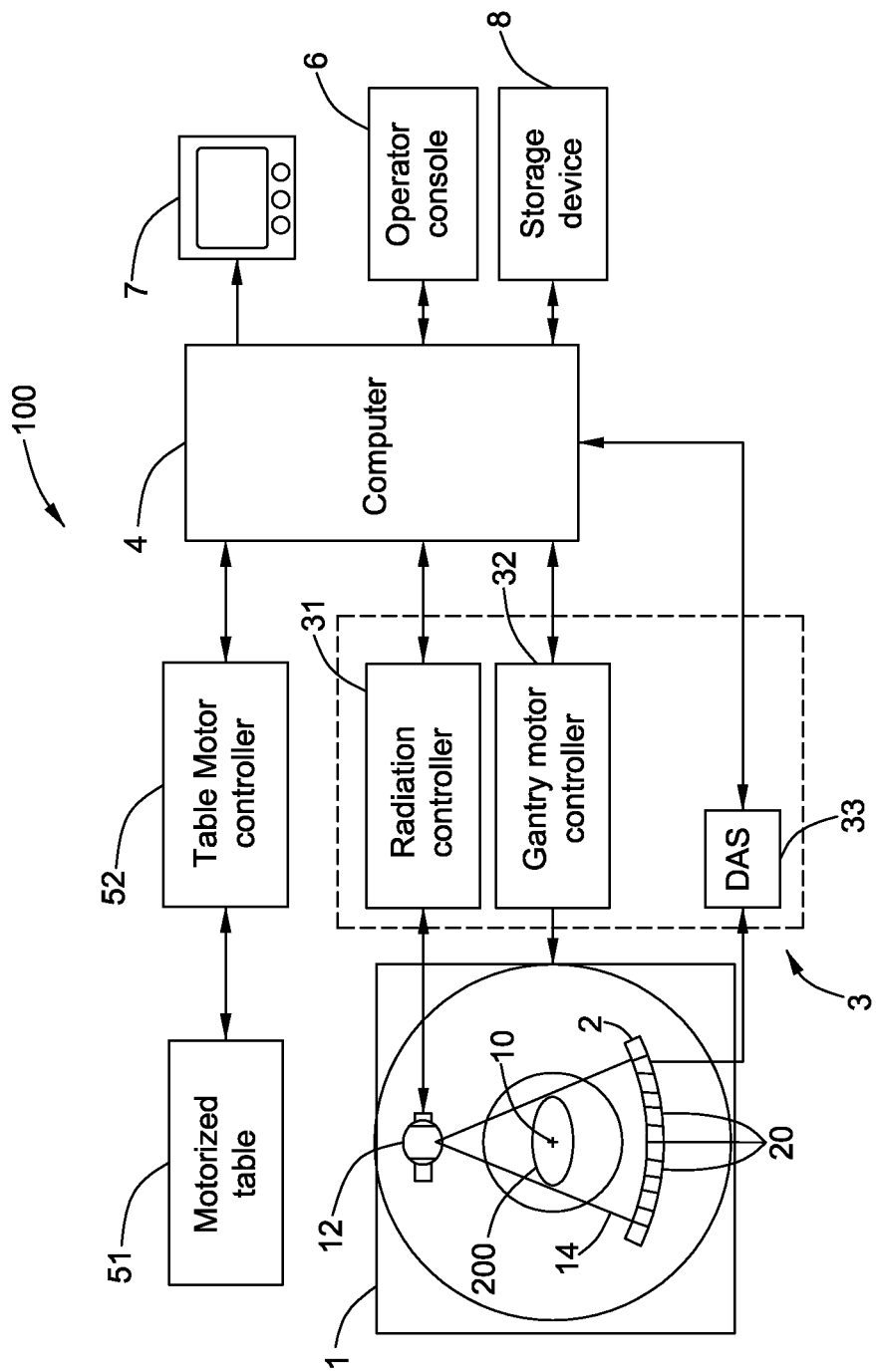
FIG. 1 is a schematic block diagram of an exemplary CT imaging system in accordance with an embodiment of the present disclosure.

FIG. 1 illustrates a schematic block diagram of an exemplary imaging system 100 in accordance with one embodiment of the present disclosure. As shown in FIG. 1, the exemplary imaging system 100, for example, a CT (computed tomography) imaging system may include a gantry 1. The gantry 1 has a radiation source 12 that projects an X-ray beam 14 of X-rays toward a detector array 2 on an opposite side of the gantry 1.

The detector array 2 may be formed by a plurality of detectors 20 which together sense the projection beams 14 that pass through an object 200 including multiple materials, such as a patient. Each detector 20 may produce an electrical signal that represents the total intensity of each projection beam 14 of the X-rays passing through the object 200. The detector array 2 may detect a total intensity of single-energy X-rays passing through the object 200, and may also detect a total intensity of each of multi-energy X-rays such as dual energy X-rays, which may be known as intensity series of multi-energy X-rays.

During a scan to acquire projection data relating to the detected X-rays, the gantry 1 and the components mounted thereon may rotate about a center of rotation 10.

Rotation of the gantry 1 and operation of the radiation source 12 may be governed by a control mechanism 3 of the CT imaging system 100. The control mechanism 3 may include a radiation controller 31 that provides power and timing signals to the radiation source 12 and a gantry motor controller 32 that controls the rotational speed and position of the gantry 1. A data acquisition system (DAS) 33 in the control mechanism 3 may sample analog data from the plurality of detectors 20 and convert the analog data to digital signals for subsequent processing.

A computer 4 may also receive commands and scanning parameters from an operator via an operator console 6. The operator supplied commands and parameters are used by the computer 4 to provide control signals and information to the DAS 33, the radiation controller 31, and the gantry motor controller 32. In addition, the computer 4 may operate a table motor controller 52 which controls a motorized table 51 to position the object 200 in the gantry 1. The motorized table 51 may move portions of the object 200 through an opening (not labeled) of the gantry 1.

The computer 4 may receive sampled and digitized radiation data from the DAS 33, and perform corresponding processing to reconstruct an X-ray image volume. An associated display 7 allows the operator to observe the reconstructed image $I_{mg}$ and other data from the computer 4. The computer 4 may store the reconstructed image $I_{mg}$ in a storage device 8.

The computer 4 of the present disclosure may obtain basis material information of the multiple materials based on the detected total intensity of the X-rays. Obtaining the basis material information of the multiple materials may include obtaining projection data of at least one of a path length, an integral of a linear attenuation coefficient, and an integral of a density distribution of each of the multiple materials for each projection beam 14 of the X-rays.

Alternatively, the computer 4 of the present disclosure may obtain basis component information of photon-electric absorption basis component and Compton scattering basis component of the object 200 based on the detected total intensity of the X-rays. The basis component information of photon-electric absorption basis component and Compton scattering basis component of the object 200 may be obtained from the material decomposition.

The detected total intensity of the X-rays mentioned in the present disclosure should be intended to include the detected total intensity of single-energy X-rays, or the detected total intensity of each of multi-energy X-rays (i.e. intensity series of multi-energy X-rays).

Hereinafter, how the computer 4 obtains at least one set of basis information of the basis material information and the basis component information based on the detected total intensity of the X-rays will be described in detail with reference to FIGS. 5-6.

Figure 5:
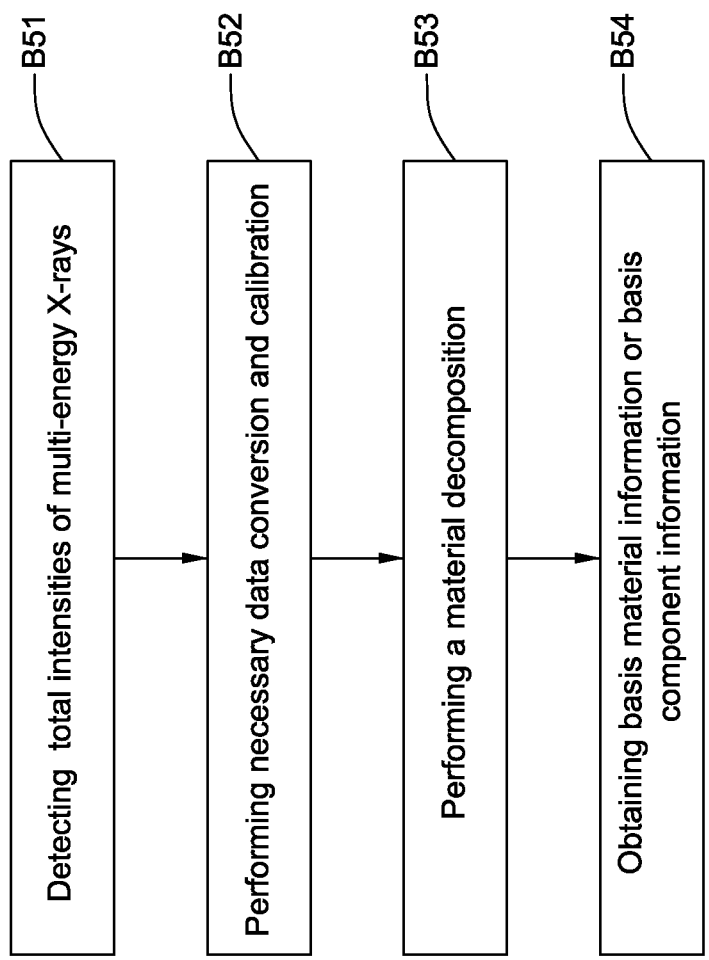
FIG. 5 illustrates steps how to obtain at least one set of basis information in accordance with an embodiment of the present disclosure.

FIG. 5 illustrates one embodiment of obtaining the at least one set of basis information. In block B51 of FIG. 5, the total intensity of each of multi-energy X-rays passing through the object 200 comprising the multiple materials may be detected by the detector 20. As an example, the detected multiple total intensities (also known as intensity series) of the multi-energy X-rays may include dual energy X-ray measurements comprising low-energy X-ray measurements and high-energy X-ray measurements. Specifically, the detector 20 may detect a total intensity of low-energy X-rays passing through the object 200 comprising the multiple materials, and detecting a total intensity of high-energy X-rays passing through the object 200 comprising the multiple materials.

In an optional block B52, a necessary data conversion and calibration may be performed for the detected total intensity of each of the multi-energy X-rays. For example, a data conversion and calibration may be performed for the total intensity of the low-energy X-rays, and a data conversion and calibration may be performed for the total intensity of the high-energy X-rays.

In block B53, a material decomposition may be performed based on the detected total intensity of each of the multi-energy X-rays. For example, the material decomposition may be performed based on the detected total intensity of the low-energy X-rays and the detected total intensity of the high energy X-ray. In an embodiment where block B52 is included, the material decomposition process may be performed based on the calibrated total intensity of the low-energy X-rays and the calibrated total intensity of the high-energy X-rays.

In block B54, the basis material information of the multiple materials or the basis component information of the object 200 may be obtained after the material decomposition of block B53.

Figure 6:
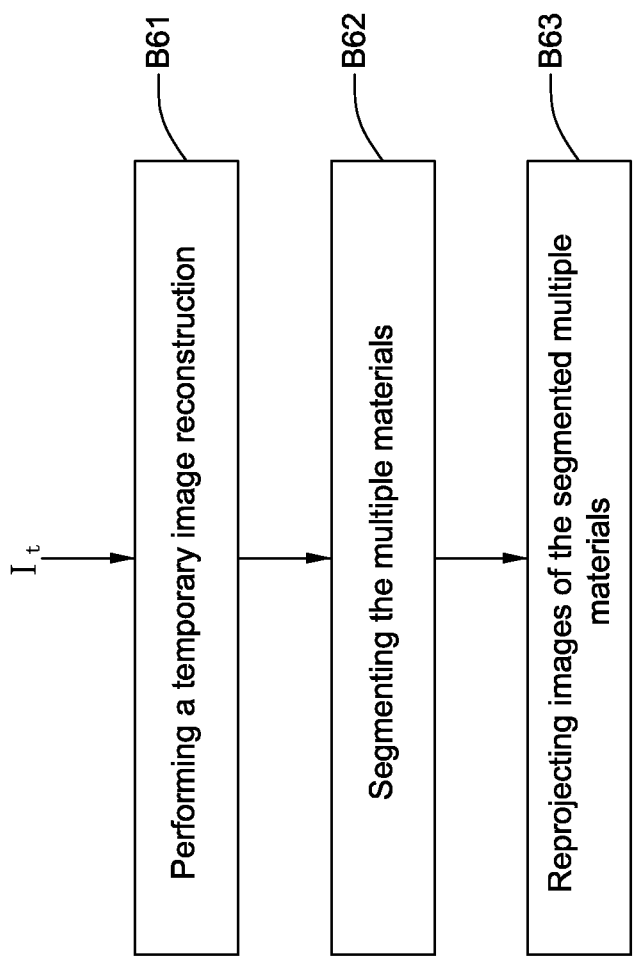
FIG. 6 illustrates steps how to obtain at least one set of basis information in accordance with another embodiment of the present disclosure.

FIG. 6 illustrates another embodiment of obtaining the basis material information of the multiple materials. In block B61 of FIG. 6, a temporary image reconstruction may be performed based on the detected total intensity $I_t$.

In block B62, the multiple materials may be segmented based on the temporary image reconstruction.

In block B63, images of the segmented multiple materials may be reprojected so as to obtain projection data, path lengths or path length sequences for the multiple materials. The projection data, the path lengths or the path length sequences for the multiple materials may represent the basis material information of the multiple materials.

The basis material information of the multiple materials may comprise projection data, a path length or a path length sequence of each of the multiple materials for each projection beam 14 of the X-rays. In yet another embodiment, the projection data, the path length or the path length sequence of each of the multiple materials for each projection beam 14 of the X-rays may also be obtained from direct segmentation of projection data of the detected total intensity $I_t$.

The computer 4 may perform a scatter correction using the basis material information or the basis component information after obtaining the basis material information of the multiple materials or the basis component information of photon-electric absorption basis component and Compton scattering basis component. The scatter correction performed by using the basis component information is similar to the scatter correction performed by using the basis material information.

Hereinafter, how the computer 4 performs the scatter correction using the basis material information of the multiple materials or the basis component information of the object 200 will be described in detail with reference to FIGS. 2-3.

Figure 2:
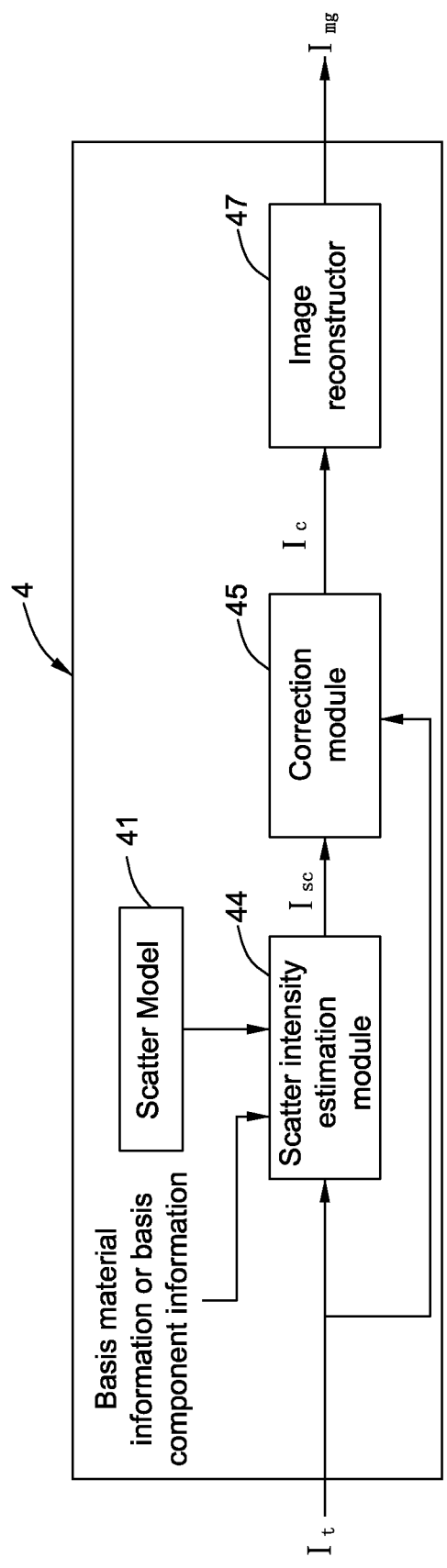
FIG. 2 is a schematic block diagram of one embodiment of modules executing in a computer of FIG. 1.

FIG. 2 illustrates a schematic block diagram of modules executing in the computer 4 in accordance with one embodiment of the present disclosure. As shown in FIG. 2, the computer 4 may include a scatter model 41 and a scatter intensity estimation module 44. In one embodiment, the scatter model 41 may be in association with the basis material information of the multiple materials. In this embodiment, the multiple materials may be characterized by a low effective atomic number material and a high effective atomic number material. The low effective atomic number material may for example include a soft tissue. The high effective atomic number material may for example include at least one of bone, a metal and a contrast agent such as iodine. Alternatively, in the embodiment using the basis component information, the scatter model 41 may be in association with the basis component information of photo-electric absorption basis component and Compton scattering basis component of the object 200.

The scatter intensity estimation module 44 may use a scatter model 41 according to the obtained basis material information of the multiple materials and the detected total intensity of the X-rays $I_t$ to estimate the scatter intensity component $I_{sc}$. The basis material information of the multiple materials may include projection data of the basis material information used to characterize the multiple materials along each projection beam 14 of the X-rays. Alternatively, in the embodiment using the basis component information, the scatter intensity estimation module 44 may use the scatter model 41 according to the obtained basis component information of photo-electric absorption basis component and Compton scattering basis component of the object 200 and the detected total intensity of the X-rays $I_t$ to estimate the scatter intensity component $I_{Sc}$.

The scatter model 41 may be established based on the detected total intensity $I_t$ and the obtained projection data of the basis material information of each material along each projection beam 14.

For example, in one embodiment, the scatter model 41 may include the following equation:

$$I_{sc} = K I_t^{f_1(p_l, p_h)} \left(-\log\left(\frac{I_t}{I_0}\right)\right)^{f_2(p_l, p_h)} \quad (1)$$

where $I_{sc}$ represents the estimated scatter intensity component, $I_t$ represents the detected total intensity of the X-rays in the scan of the object 200, $I_0$ represents a detected total intensity of the X-rays in an air scan without the object 200, $p_l$ represents projection data for the low effective atomic number material, $p_h$ represents projection data for the high effective atomic number material, $f_1$ and $f_2$ represent functions of $p_l$ and $p_h$, K represents a constant scaling factor, and $p_l$ and $p_h$ may characterize the basis material information of the low and the high effective atomic number materials.

Thus, the scatter intensity estimation module 44 may use the detected total intensity $I_t$, the detected total intensity $I_0$ without the object 200, and the projection data $p_l$ and $p_h$ for the low and the high effective atomic number materials from the scatter model 41 to estimate the scatter intensity component $I_{sc}$.

In another embodiment, the scatter model 41 may include the following equation:

$$I_{sc} = K I_t^{a_1 + a_2 \frac{p_h}{p_l}} \left(-\log\left(\frac{I_t}{I_0}\right)\right)^{b_1 + b_2 \frac{p_h}{p_l}} \quad (2)$$

Where K, $a_1$, $a_2$, $b_1$ and $b_2$ are tuned parameters for the low and the high effective atomic number materials respectively.

In still another embodiment, the scatter model 41 may include the following equation:

$$I_{sc} = K_l I_t^{a_l} p_l^{b_l} + K_h I_t^{a_h} p_h^{b_h} \quad (3)$$

Where $K_1$, $a_1$, $b_1$, $K_h$, $a_h$ and $b_h$ are tuned parameters for the low and the high effective atomic number materials respectively.

The equations (1)-(3) above are only illustrative examples of the scatter model 41. However, the scatter model 41 of the present disclosure should be not limited hereinto. The scatter model 41 incorporating the material information would be covered in the protection scope of the present disclosure.

The computer 4 may include a correction module 45. The correction module 45 may receive the estimated scatter intensity component $I_{sc}$ and the detected total intensity $I_t$, and obtain an intensity estimate $I_c$ of primary X-rays incident on a detector 20 based on the detected total intensity $I_t$ and the estimated scatter intensity component $I_{sc}$. As an example, the primary intensity estimate $I_c$, may be obtained by subtracting the estimated scatter intensity component $I_{sc}$ from the detected total intensity $I_t$.

The computer 4 may include an image reconstructor 47. The image reconstructor 47 may receive the primary intensity estimate $I_c$, output by the correction module 45, and may reconstruct an X-ray image $I_{mg}$ using the obtained primary intensity estimate $I_c$.

A material decomposition process with improved accuracy can be performed again to provide projection data of the basis material information of each material for image reconstruction.

Figure 3:
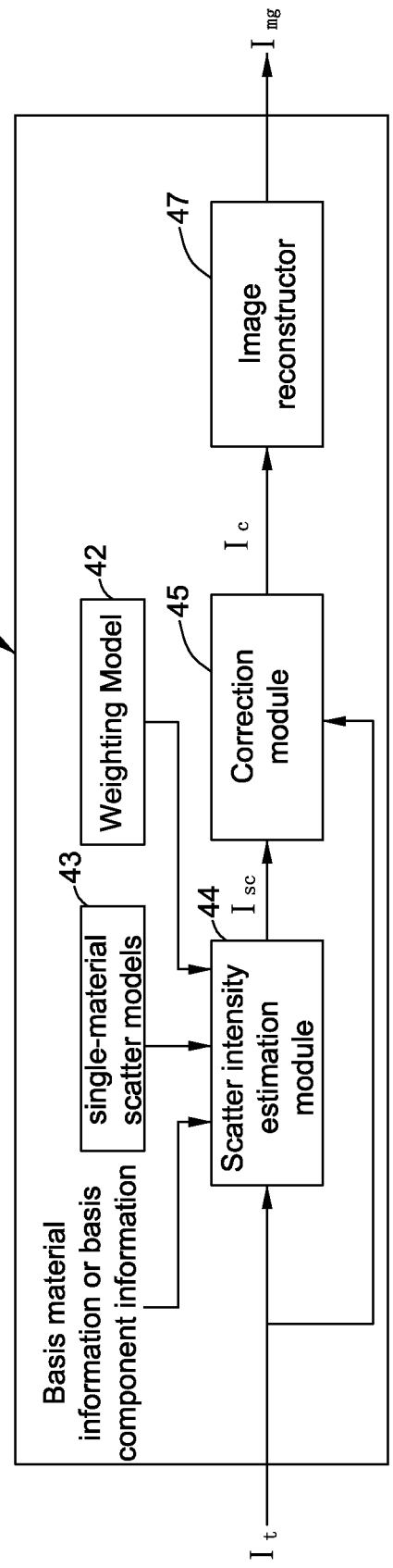
FIG. 3 is a schematic block diagram of another embodiment of modules executing in the computer of FIG. 1.

FIG. 3 illustrates a schematic block diagram of modules executing in the computer 4 in accordance with another embodiment of the present disclosure. As shown in FIG. 3, the computer 4 may include a weighting model 42, single-material scatter models 43 and a scatter intensity estimation module 44.

The scatter intensity estimation module 44 may use a weighting model 42 to weight the basis material information of the multiple materials (for example, the obtained projection data of each of the multiple materials), determine a scatter intensity component of each material, $I_{sc,i}$, based on individual single-material scatter models 43 for each material, weight the scatter intensity component of each material, $I_{sc,i}$, determined by the single-material scatter models 43 with the weighted projection data of each material, and estimate the scatter intensity component $I_{sc}$ of the detected X-rays based on the weighted scatter intensity component of each material.

In one embodiment, the weighting model 42 may include the following equations:

$$w_i = \frac{p'_i}{\sum_i p'_i} \quad (4)$$

$$p'_i = p_i \times \sum_E (S_E \times f(\varepsilon_{sc,i,E}, \varepsilon_{i,E})) \quad (5)$$

Where $w_i$ represents a weighting factor of each material determined by equation (4), i represents the index of material, $p_i'$ represents a weighted projection data of each material determined by equation (5), $p_i$ represents the projection data of each material obtained in the material decomposition process, $S_E$ represents an X-ray intensity of the spectrum at energy E of the X-rays, $\varepsilon_{sc,i,E}$ represents a sum of cross-sections of Compton scattering and Rayleigh scattering of each material at energy E, $\varepsilon_{i,E}$ represents a total cross-section of X-ray processes of each material at energy E, and f represents a function of $\varepsilon_{sc,i,E}$ and $\varepsilon_{i,E}$.

The individual single-material scatter models 43 for each material may include the following equation:

$$I_{sc,i} = k_i I_t^{m_i} \left(-\log\left(\frac{I_t}{I_0}\right)\right)^{n_i} \quad (6)$$

Where $I_{sc,i}$ represents a scatter intensity component of each material obtained by individual single-material scatter models 43 for each material, $I_t$ represents the detected total intensity of the X-rays in the scan of the object 200, $I_0$ represents a detected total intensity of the X-rays in an air scan without the object 200, and $k_i$, $m_i$ and $n_i$ are tuned parameters for the single-material scatter models 43.

The scatter intensity estimation module 44 may receive the detected total intensity $I_t$, the obtained basis material information of the multiple materials, the weighting factor $w_i$ of each material and the scatter intensity component of each material, $I_{sc,i}$, obtained by individual single-material scatter models 43 for each material, and estimate the scatter intensity component $I_{sc}$ according to the following equation:

$$I_{sc} = \Sigma_i (I_{sc,i} \times w_i) \quad (7)$$

Because the basis component information and the basis material information can be converted to each other using some simple transfer function, the method executed in modules of FIG. 3 may be similarly applied to the basis component information.

The system 100 of the present disclosure may perform the scatter correction using the basis material information of the multiple materials or the basis component information of the object 200 and solve the multiple material problem of fast scatter estimation and correction. Therefore, the system 100 of the present disclosure may reduce greatly or even eliminate artifacts caused by the scatter and improve the image quality and quantitative measurement of Hounsfield Units (HU) of the reconstructed images.

Figure 4:
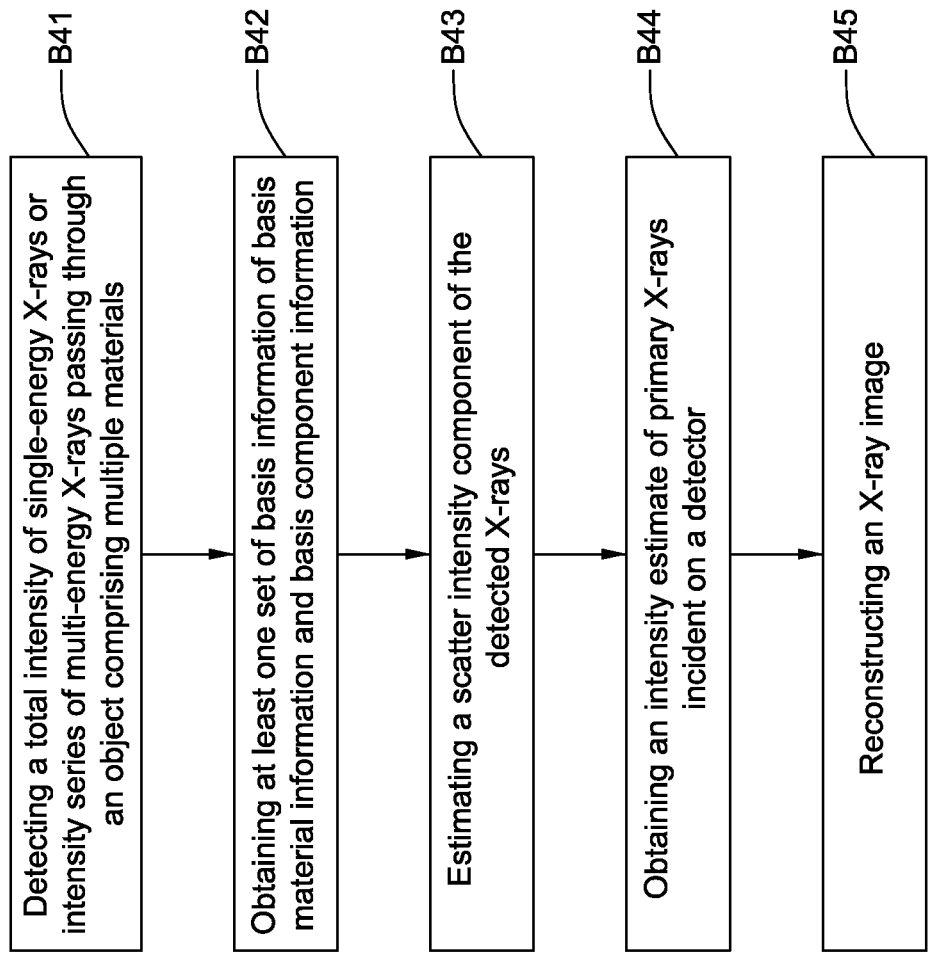
FIG. 4 is a flow chart of an exemplary signal processing method in accordance with an embodiment of the present disclosure.

The present disclosure may further provide a signal processing method. FIG. 4 illustrates a flow chart of an exemplary signal processing method in accordance with an embodiment of the present disclosure.

As shown in FIG. 4, in block B41, a total intensity or intensity series $I_t$ of X-rays may be detected passing through an object 200 comprising multiple materials with single or multiple scans at single or multiple energies.

In block B42, at least one set of basis information of basis material information of the multiple materials and basis component information of photon-electric absorption basis component and Compton scattering basis component of the object 200 may be obtained. The basis material information of the multiple materials may be obtained for example with reference to the methods shown in FIGS. 5-6. The basis material information of the multiple materials may include projection data of at least one of a path length, an integral of the linear attenuation coefficient, and an integral of the density distribution of each of the multiple materials along each projection beam 14 of the X-rays. The basis component information of photon-electric absorption basis component and Compton scattering basis component of the object 200 may be obtained from the material decomposition.

In block B43, a scatter intensity component $I_{sc}$ of the detected X-rays may be estimated based on the at least one set of basis information and the detected total intensity $I_t$.

In block B44, an intensity estimate of primary X-rays $I_c$, incident on a detector 20 may be obtained based on the detected total intensity $I_t$ and the estimated scatter intensity component $I_{sc}$. The intensity estimate of primary X-rays $I_c$ may be obtained by subtracting the estimated scatter intensity component $I_{sc}$ from the detected total intensity $I_t$.

In block B45, an X-ray image $I_{mg}$ may be reconstructed using the obtained primary intensity estimate $I_c$.

The method of the present disclosure may perform the scatter correction using the basis material information of the multiple materials or the basis component information of the object 200, and solve the multiple material problems of fast scatter estimation and correction. Therefore, the method of the present disclosure may reduce greatly or eliminate artifacts caused by the scatter and improve the image quality and quantitative measurement of Hounsfield Units (HU) of the reconstructed images.

While steps of the signal processing methods in accordance with embodiments of the present disclosure are illustrated as functional blocks, the order of the blocks and the separation of the steps among the various blocks shown in FIGS. 4-6 are not intended to be limiting. For example, the blocks may be performed in a different order and a step associated with one block may be combined with one or more other blocks or may be sub-divided into a number of blocks.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A signal processing method, comprising:
    detecting a total intensity of X-rays passing through an object comprising multiple materials via a detector of a computed tomography system;
    obtaining, via a computer, at least one set of basis information of basis material information of the multiple materials and basis component information of photon-electric absorption basis component and Compton scattering basis component of the object, wherein obtaining the basis material information of the multiple materials comprises obtaining projection data of the basis material information used to characterize each of the multiple materials along each projection beam of the X-rays;
    estimating, via the computer, a scatter intensity component of the detected X-rays based on the at least one set of basis information and the detected total intensity; and
    obtaining, via the computer, an intensity estimate of primary X-rays incident on a detector based on the detected total intensity and the estimated scatter intensity component;
    wherein estimating the scatter intensity component comprises using a weighting model to weight the obtained projection data of each material, determining a scatter intensity component of each material based on individual single-material scatter models for each material, weighting the scatter intensity component of each material determined by the single-material scatter models with the weighted projection data of each material, and estimating the scatter intensity component of the detected X-rays based on the weighted scatter intensity component of each material.

2. The method of claim 1, wherein obtaining the basis material information of the multiple materials comprises obtaining projection data of at least one of a path length, an integral of a linear attenuation coefficient, and an integral of a density distribution of each of the multiple materials for each projection beam of the X-rays.

3. The method of claim 2, wherein obtaining the projection data of at least one of a path length, an integral of a linear attenuation coefficient, and an integral of a density distribution of each of the multiple materials for each projection beam of the X-rays comprises performing a material decomposition process.

4. The method of claim 1, comprising reconstructing, via the computer, an X-ray image based on the intensity estimate.

5. The method of claim 1, comprising detecting an additional total intensity of X-rays passing through air, and wherein each individual single-material scatter model utilizes the detected additional total intensity in estimating the scatter intensity component.

6. The method of claim 1, wherein each individual single-material scatter model is established based on at least the detected total intensity.

7. The method of claim 1, wherein obtaining the basis material information of the multiple materials comprises obtaining projection data, a path length or a path length sequence of each of the multiple materials for each projection beam of the X-rays, and obtaining the projection data, the path length or the path length sequence of each of the multiple materials for each projection beam of the X-rays comprises performing a temporary image reconstruction based on the detected total intensity, segmenting the multiple materials based on the temporary image reconstruction, and reprojecting images of the segmented multiple materials to obtain the projection data, the path lengths or the path length sequences for the multiple materials.

8. The method of claim 1, wherein obtaining the basis material information of the multiple materials comprises obtaining projection data, a path length or a path length sequence of each of the multiple materials for each projection beam of the X-rays from direct segmentation of projection data of the detected total intensity.

9. The method of claim 1, wherein detecting the total intensity of the X-rays passing through the object comprising the multiple materials comprises detecting a total intensity of low-energy X-rays passing through the object comprising the multiple materials, and detecting a total intensity of high-energy X-rays passing through the object comprising the multiple materials, and wherein obtaining the basis material information of the multiple materials comprises performing a material decomposition process based on the detected total intensity of the low-energy X-rays and the detected total intensity of the high energy X-ray.

10. The method of claim 9, wherein before performing the material decomposition process, the method further comprises performing data conversion and calibration for the total intensity of the low-energy X-rays, and performing data conversion and calibration for the total intensity of the high-energy X-rays, and wherein performing the material decomposition process is based on the calibrated total intensity of the low-energy X-rays and the calibrated total intensity of the high-energy X-rays.

11. The method of claim 1, wherein the multiple materials is characterized by a low effective atomic number material and a high effective atomic number material.

12. The method of claim 11, wherein the low effective atomic number material comprises a soft tissue, and the high effective atomic number comprises at least one of bone, a metal and a contrast agent.

13. A computed tomography imaging system, comprising:
a detector configured to detect a total intensity of X-rays passing through an object comprising multiple materials; and
a computer configured to obtain at least one set of basis information of basis material information of the multiple materials and basis component information of photon-electric absorption basis component and Compton scattering basis component of the object, estimate a scatter intensity component of the detected X-rays based on the at least one set of basis information and the detected total intensity, and obtain an intensity estimate of primary X-rays incident on the detector based on the detected total intensity and the estimated scatter intensity component, wherein the computer is configured to obtain the basis material information of the multiple materials by obtaining projection data of the basis material information used to characterize each of the multiple materials along each projection beam of the X-rays;
wherein the computer is configured to estimate the scatter intensity component by using a weighting model to weight the obtained projection data of each material, determining a scatter intensity component of each material based on individual single-material scatter models for each material, weighting the scatter intensity component of each material determined by the single-material scatter models with the weighted projection data of each material, and estimating the scatter intensity component of the detected X-rays based on the weighted scatter intensity component of each material.

14. The computed tomography imaging system of claim 13, wherein the computer is configured to reconstruct an X-ray image based on the intensity estimate.

15. The computed tomography imaging system of claim 13, wherein the computer is configured for performing a material decomposition process for the detected total intensity of the X-rays to obtain the projection data of at least one of a path length, an integral of the linear attenuation coefficient, and an integral of the density distribution of each of the multiple materials along each projection beam of the X-rays.

16. The computed tomography imaging system of claim 13, wherein the computer is configured for obtaining projection data, a path length or a path length sequence of each of the multiple materials for each projection beam of the X-rays, and obtaining the projection data, the path length or the path length sequence of each of the multiple materials for each projection beam of the X-rays comprises:
performing a temporary image reconstruction based on the detected total intensity;
segmenting the multiple materials based on the temporary image reconstruction; and
reprojecting images of the segmented multiple materials to obtain the projection data, the path lengths or the path length sequences for the multiple materials.

17. The computed tomography imaging system of claim 13, wherein the computer is configured for performing a material decomposition process for the detected total intensity of the X-rays to obtain projection data of the basis material information of each material for each projection beam of the X-rays.

18. The computed tomography imaging system of claim 13, wherein the multiple materials is characterized by a low effective atomic number material and a high effective atomic number material.

19. The computed tomography imaging system of claim 18, wherein the low effective atomic number material comprises a soft tissue, and the high effective atomic number comprises at least one of bone, a metal and a contrast agent.

20. The computed tomography imaging system of claim 13, wherein the detector is configured to detect an additional total intensity of X-rays passing through air, and wherein each individual single-material scatter model is configured to utilize the detected additional total intensity in estimating the scatter intensity component.

* * * * *